(12) United States Patent
Nakano

(10) Patent No.: US 8,840,599 B2
(45) Date of Patent: Sep. 23, 2014

(54) DISPOSABLE DIAPER AND ABSORBENT ARTICLE

(75) Inventor: Yuki Nakano, Sakura (JP)

(73) Assignee: Daio Paper Corporation, Ehime (JP)

( * ) Notice: Subject to any disclaimer, the term of this patent is extended or adjusted under 35 U.S.C. 154(b) by 663 days.

(21) Appl. No.: 12/452,835

(22) PCT Filed: Jul. 18, 2008

(86) PCT No.: PCT/JP2008/063009
§ 371 (c)(1),
(2), (4) Date: Jan. 25, 2010

(87) PCT Pub. No.: WO2009/014085
PCT Pub. Date: Jan. 29, 2009

(65) Prior Publication Data
US 2010/0152697 A1    Jun. 17, 2010

(30) Foreign Application Priority Data

Jul. 26, 2007  (JP) ................................ 2007-195229

(51) Int. Cl.
| A61F 13/15 | (2006.01) |
| A61F 13/494 | (2006.01) |
| A61F 13/56 | (2006.01) |
| A61F 13/49 | (2006.01) |
| A61F 13/515 | (2006.01) |

(52) U.S. Cl.
CPC ......... *A61F 13/515* (2013.01); *A61F 13/49413* (2013.01); *A61F 13/5622* (2013.01); *A61F 13/49017* (2013.01); *A61F 13/49019* (2013.01)
USPC .................. 604/385.23; 604/385.24; 604/389

(58) Field of Classification Search
CPC ......... A61F 13/15; A61F 13/45; A61F 13/58; A61F 13/72; A61F 5/44; A41B 13/04
USPC ........... 604/385.23, 385.24, 385.27, 389, 367
See application file for complete search history.

(56) References Cited

FOREIGN PATENT DOCUMENTS

| EP | 0382022 A2 | 8/1990 |
| EP | 1197195 A1 | 4/2002 |
| EP | 1327432 A2 | 7/2003 |
| JP | 2000-300602 | 10/2000 |
| JP | 2002-45399 | 2/2002 |
| JP | 2003-88547 | 3/2003 |
| JP | 2003-126141 | 5/2003 |
| JP | 2004-24308 | 1/2004 |
| JP | 2004-49765 | 2/2004 |
| JP | 2005-192814 | 7/2005 |
| JP | 2005-287791 | 10/2005 |
| JP | 2005-323780 | 11/2005 |
| JP | 2007-97619 | 4/2007 |
| JP | 2007-97627 | 4/2007 |
| JP | 2007-185329 | 7/2007 |

*Primary Examiner* — Tatyana Zalukaeva
*Assistant Examiner* — Benedict L Hanrahan
(74) *Attorney, Agent, or Firm* — DLA Piper LLP (US)

(57) ABSTRACT

A disposable diaper in the present invention is configured in such a manner that a section corresponding to a first portion at the longitudinal intermediate of the inner elastic members is designated as an unfixed section where a back sheet and an outer sheet are not fixed; a section corresponding to a second portion on the both longitudinal sides of the unfixed section is designated as a fixed section, where the back sheet and the outer sheet are fixed; the unfixed section with the inner elastic members is not fixed to the back sheet or the outer sheet, or is fixed only to the outer sheet; and the fixed section with the inner elastic members is fixed to the back sheet and the outer sheet.

6 Claims, 14 Drawing Sheets

DISPOSABLE DIAPER AND ABSORBENT ARTICLE

TECHNICAL FIELD

The present invention relates to a disposable diaper and an absorbent article having the disposable diaper and an absorbent pad.

BACKGROUND ART

An absorbent article has an elongated elastic member such as a rubber thread that is adhered and fixed in a stretched state at an appropriate position so as to be enhanced in a property of fitting to the body of a wearer. In a tape-type disposable diaper, for example, a plurality of elongated elastic members is adhered and fixed in a front-back direction to an under side of an absorbent body on both sides of the diaper in the width direction, thereby to increase the absorbent body in a property of fitting to the body of a wearer.

Meanwhile, a disposable diaper for adults in particular, uses generally an absorbent pad on an inner surface thereof for absorption of urine in consideration of the frequency of diaper replacement (refer to Patent Documents 1 to 5, for example). In such a usage, an elastic member on an under side of the absorbent body in the diaper is utilized to fit the absorbent pad to the body of a wearer.

Patent Document 1: JP 2004-024308 A
Patent Document 2: JP 2005-287791 A
Patent Document 3: JP 2007-097619 A
Patent Document 4: JP 2007-097627 A
Patent Document 5: JP 2003-088547 A

DISCLOSURE OF THE INVENTION

Technical Problem to be Solved

However, such a conventional diaper may have an absorbent pad displaced or deformed (contracted, twisted, or the like) by body movements of a wearer. Such a displaced or deformed absorbent pad may undesirably cause leakage.

Therefore, a principal object of the present invention is to prevent an absorbent pad from being displaced or deformed by body movements of a wearer, thereby avoiding leakage.

Means to Solve the Problem

The inventor's earnest studies on the foregoing problem have produced findings as described below. Specifically, a conventional diaper has an elastic member fixed entirely in the longitudinal direction to an under side of an absorbent body. Accordingly, as the diaper is displaced or deformed, the elastic member fixed to the under side of the absorbent body is also moved and displaced from a position suitable for pressing the absorbent pad against the body of a wearer, and becomes unbalanced in a stretching force. As a result, the absorbent pad is not properly pressed against the body of the wearer, and is likely to be displaced or deformed. On the basis of the foregoing findings, the present invention has been devised as described below.

<Invention According to Claim 1>

A disposable diaper comprising:
an outer part having a crotch portion and ventral and back side portions extending to front and back sides of the crotch portion, respectively; and
an inner part provided on an inner surface of the outer part, the outer part being formed by sticking an inner sheet to on an inside of an outer sheet and the inner part being fixed to an inner surface of the inner sheet,
the inner part having an absorbent body at a section containing the crotch portion, and
an elongated elastic member being fixed between the inner and outer sheets on both sides in a width direction so as to extend from the ventral side portion through the crotch portion to the back side portion, wherein
out of a first portion in a longitudinal intermediate of the elongated elastic member and a second portion on both longitudinal sides of the first portion, a section in the diaper corresponding to the first portion is designated as an unfixed section where the inner and outer sheets are not fixed, and a section corresponding to the second portion is designated as a fixed section where the inner and outer sheets are fixed,
the elongated elastic member in the unfixed section is not fixed to the inner or outer sheet or is fixed only to the outer sheet, and
the elongated elastic member in the fixed section is fixed to the inner and outer sheets.

(Effect and Operation)

In the present invention, the elastic member can move singly or together with the outer sheet with respect to the inner sheet in the unfixed section. Accordingly, even if the inner sheet and the inner part are deformed by body movements, for example, the elastic member is not affected by the deformation and is kept in a proper position or in a properly stretched position, thereby to press the absorbent pad on the inner surface of the inner part against the body of the wearer in a proper position or in a properly stretched state. Therefore, the present invention makes the absorbent pad less prone to be displaced or deformed (contracted, twisted, or the like) by body movements of the wearer, which suppresses leakage resulting from such a displacement or the like.

In particular, when the wearer moves his/her legs, the absorbent pad is likely to be displaced because the diaper is changed in shape around his/her thighs due to swells and depressions in inner thigh muscles (adductor muscles). In addition, if the wearer is a person with a nonstandard body type wear such as an obese person with a narrower space between the legs, a lean person with a wider space between the legs, or an elderly person with sagging buttocks, the diaper is more prone to be displaced or deformed, resulting in displacements of the absorbent pad. According to the present invention, even in such cases, the absorbent pad is unlikely to be displaced owing to the foregoing effect.

<Invention According to Claim 2>

The disposable diaper according to claim 1, wherein
the unfixed section is continuously provided ranging from a position of 150 to 250 mm frontward with respect to a center of the diaper in a front-back direction to a position of 10 to 160 mm backward with respect to the center of the diaper in the front-back direction.

(Effect and Operation)

In the invention of this claim, the unfixed section in the front-back direction of the diaper covers the crotch portion and its neighborhood portions in the front-back direction. These portions are sandwiched between the both legs and are under forces from various directions caused by twists and the like mainly due to widthwise contraction, and therefore the elastic member is likely to be displaced from the proper position. Accordingly, by setting the unfixed section at those portions, it is possible to prevent effectively displacement or deformation of the absorbent pad.

<Invention According to Claim 3>

The disposable diaper according to claim 1, wherein the unfixed section is continuously provided in the front-back direction, in a front-back area of ±10 to 40 mm with reference to a position of 170 to 210 mm frontward with respect to the center of the diaper in the front-back direction, and the other unfixed section is continuously provided in a front-back area of ±20 to 30 mm with reference to a position of 20 to 50 mm backward with respect to the center of the diaper in the front-back direction.

(Effect and Operation)

In the invention of this claim, the unfixed section in the front-back direction of the diaper covers an inguinal region, gluteal sulcus and their neighborhood areas. The diaper may have relatively large shape changes at the inguinal region and its neighborhood areas, and may have large extension or contraction at the gluteal sulcus and their neighborhood areas, and therefore the elastic member is likely to be displaced from the proper position in those areas. Accordingly, by setting the unfixed sections in those areas, it is possible to prevent effectively displacement or deformation of the absorbent pad.

<Invention According to Claim 4>

The disposable diaper according to any one of claims 1 to 3, wherein the unfixed section extends, on at least one of a widthwise outside and a widthwise inside with respect to an elongated elastic member running in the section, in a direction orthogonal to the elongated elastic member by a distance equal to or more than a full width of the elongated elastic member.

(Effect and Operation)

In the present invention, the elastic member may be made movable only in the longitudinal direction (in this case, since extension and contraction of the elastic members are freed from the inner sheet, the diaper is less prone to be stretched in an unbalanced manner) and the unfixed section may be formed narrower so as not to move in the direction orthogonal to the longitudinal direction of the elastic member. However, it is preferred that the unfixed section is configured in such a manner as to form a certain movable space (width) in the direction orthogonal to the longitudinal direction of the elastic member, as described in this claim. Accordingly, the elastic member can be kept in a proper position and in a proper stretched state, thereby further enhancing the above-mentioned effect of the present invention. In addition, the full width of the elongated elastic member in the present invention refers to a width of one elongated elastic member if the elastic member is provided alone, or refers to a sum of widths of a plurality of elongated elastic members if those elastic members are provided together.

<Invention According to Claim 5>

The tape-type disposable diaper according to any one of claims 1 to 4, wherein a fastening tape is projected from both sides in the width direction of at least one of the ventral and back side portions, for connection with the other portion in a detachable manner.

(Effect and Operation)

As described in this claim, tape-type disposable diapers are apt to be insufficient in a property of fitting to the body of the wearer and cause displacements of the absorbent pad, and therefore are particularly suitable as a target of the present invention.

<Invention According to Claim 6>

An absorbent article comprising:

the disposable diaper according to any one of claims 1 to 5;

an absorbent pad having front and back portions extending to front and back sides of the crotch portion, respectively, and an absorbent body formed of a fiber assembly at a main body part surrounded by a circumferential portion, wherein the absorbent pad is disposed in alignment with the crotch portion on an inner surface of the inner part of the disposable diaper.

(Effect and Operation)

The foregoing effects and operations in the present invention can be produced.

Advantage of the Invention

As stated above, according to the present invention, the absorbent pad is less prone to be displaced or deformed (contracted, twisted, or the like) by body movements of a wearer, thereby to suppress advantageously occurrence of leakage resulting from such a displacement and the like.

Best Mode for Carrying Out the Invention

One embodiment of the present invention will be described below in detail with reference to the attached drawings. In the present invention, the "crotch portion" refers to a portion of a diaper that fits to the crotch of a wearer, and constitutes a front-back central portion and its front-back neighborhood portions in most diapers. Specifically, in a diaper for adults, the crotch portion ranges from 220 mm frontward to 30 mm backward with reference to the central portion of the diaper in the front-back direction. In addition, the "ventral side portion" and "front portion" refer to the portions in front of the crotch portion, and the "back side portion" and "back portion" refer to the portions in back of the crotch portion.

(Absorbent Pad)

FIGS. 1 to 4 show one example of an absorbent pad 200. The absorbent pad 200 is intended for use on an inner surface of a disposable diaper 100, and has a crotch portion C2, and a front side portion F2 and a back portion B2 extending on both sides of the crotch portion C2. Dimensions of those portions can be decided as appropriate. For example, a full length (front-back length) L1 of the pad may be about 450 to 630 mm, a full width W1 of the same may be about 135 to 320 mm (however, W1 needs to be narrower than a width of an absorbent surface of the diaper). In this case, a front-back length of the crotch portion C2 may be about 150 to 180 mm, a front-back length of the front portion F2 may be about 120 to 200 mm, and a front-back length of the back portion B2 may be about 180 to 280 mm.

The absorbent pad 200 has a basic structure in which an absorbent body 23 is interposed between an inner surface of a liquid impervious back sheet 21, on an external surface of which an outer sheet 32 is layered, and a liquid pervious top sheet 22.

Basically the absorbent body 23 uses accumulated pulp fibers, an assembly of filaments of cellulose acetate or the like, or a nonwoven fabric, to which high-absorbent polymers may be mixed and fixed as required. If necessary, the absorbent body 23 may be wrapped with crepe paper (not shown). The absorbent body 23 may be formed in any of appropriate shapes such as a band which is larger in width in a front side than a back side, a rectangular, a trapezoid, and the like. In the illustrated embodiment, the absorbent body 23 has a single-layer structure, but may have a two-layer structure in which an upper absorbent body is layered on a lower absorbent body. In the case of the two-layer structure, two layers 23U and 23B may be identical in dimensions, or may employ an illustrated structure as appropriate in which the upper absorbent body 23U is smaller in length and width than 23B and is located more frontward than 23B, or the like.

A basis weight of fibers and a basis weight of absorbent polymers in the absorbent body 23 can be decided as appropriate. A preferred basis weight of fibers is about 200 to 600 g/m², and a preferred basis weight of absorbent polymers is about 100 to 300 g/m².

The liquid impervious back sheet 21 is disposed on an under side of the absorbent body 23 so as to extend slightly beyond a circumference of the absorbent body 3. The liquid impervious back sheet 21 may use a polyethylene film, or may use a sheet with both moisture permeability and water imperviousness, from the viewpoint of stuffiness prevention. The water-impervious and moisture-permeable sheet may be a microporous sheet obtained by melting and kneading an inorganic filling material into an olefin resin such as polyethylene, polypropylene or the like to thereby form a sheet and then extending the sheet in a uniaxial or biaxial direction, for example.

In addition, an external surface of the liquid impervious back sheet 21 is covered with an outer sheet 32 made of a nonwoven fabric. The outer sheet 32 extends by a predetermined extension width beyond a circumference of the back sheet 21. The outer sheet 32 may use any of various nonwoven fabrics. Raw materials for constituting the nonwoven fabric may be any of synthetic fibers based on olefin such as polyethylene or polypropylene, polyester, amide or the like, recycled fibers such as rayon or cupra, natural fibers such as cotton.

A top surface of the absorbent body 23 is covered with the liquid pervious top sheet 22. In the illustrated embodiment, the absorbent body 23 partly extends beyond a side edge of the top sheet 22, but the top sheet 22 may be made wider so that the absorbent body 3 does not extend beyond it. The top sheet 22 uses a porous or nonporous nonwoven fabric, a perforated plastic sheet, or the like. Raw materials for constituting the nonwoven fabric may be any of synthetic fibers based on olefin such as polyethylene or polypropylene, polyester, amide or the like, recycled fibers such as rayon or cupra, natural fibers such as cotton.

At both end portions of the absorbent pad 200 in the front-back direction, the outer sheet 32 and the liquid pervious top sheet 22 extend to both front-back sides of the front and back ends of the absorbent body 23, and the outer sheet 32 and the liquid pervious top sheet 22 are stuck together to form end flap portions EF in the absence of the absorbent body 23. At both lateral sides of the absorbent pad 200, the outer sheet 32 extends outward beyond the side edges of the absorbent body 23. In addition, barrier sheets 24 have widthwise outside sections 24x stuck to entire inner surfaces of sections ranging from the extending portions of the outer sheet 32 to side portions of the top sheet 22 in the front-back direction, thereby to form side flap portions SF in the absence of the absorbent body 23. Those stuck sections, as shown in a dot pattern in FIGS. 3 and 4, are formed with a hot-melt adhesive or by heat sealing or ultrasonic sealing. Those end flap sections EF and the side flap sections SF constitute a circumferential section of the present invention, and a section surrounded by those sections constitutes a main section of the present invention. If the outer sheet 32 is not provided, the liquid impervious back sheet 21, instead of the outer sheet 32, may extend to the side flap sections SF to thereby form an external surface of the side flap sections SF.

The barrier sheets 24 may use a plastic sheet or a melt-blown nonwoven fabric as a material, and preferably use a water-repellent nonwoven fabric by silicon or the like, from the viewpoint of a favorable texture.

The barrier sheets 24 have widthwise central sections 24c extending over the top sheet 22. At ends of the widthwise central sections 24c, elongated elastic members 24G are fixed in a stretched state in the front-back direction with a hot-melt adhesive or the like. The elongated elastic members 24G may be formed in the shape of a thread, a string, a band, or the like, and use any of common materials such as styrene-based rubber, olefin-based rubber, urethane-based rubber, ester-based rubber, polyurethane, polyethylene, polystyrene, styrene-butadiene, silicon, polyester, or the like.

In the two barrier sheets 24 and 24, the widthwise outside sections 24x are stuck and fixed to the entire inner surface of the article (in the illustrated embodiment, the top surface of the top sheet 22 and the inner surface of the outer sheet 32) in the front-back direction, and the widthwise central sections 24c are stuck and fixed to the inner surface of the article (in the illustrated embodiment, the top surface of the top sheet 22) at the both ends in the front-back direction and are not fixed to the inner surface of the article (in the illustrated embodiment, the top surface of the top sheet 22) between the both ends in the front-back direction. As shown in FIG. 4, those unfixed portions constitute barrier parts that can be erected with respect to the inner surface of the article (in the illustrated embodiment, the top surface of the top sheet 22). The barrier parts have base ends 24b located in boundaries between the widthwise outside fixed portions 24x and the inside portions 24c in the barrier sheets 24.

(Tape-Type Disposable Diaper)

FIGS. 5 to 10 show one example of a tape-type disposable diaper 100 in the present invention. FIG. 11 shows an absorbent pad 200 arranged on an inner surface of the diaper 100 (the top surface of the top sheet 22). The disposable diaper 100 has a basic structure in which an absorbent body 3 is interposed between an inner surface of a liquid impervious back sheet 1, on an external surface of which an outer sheet 12 is layered, and a liquid pervious top sheet 2. In this structure, the outer sheet 12 is equivalent to an outer sheet of the subject invention, the liquid impervious back sheet 1 is equivalent to an inner sheet of the subject invention, and a layered body of the outer sheet 12 and the liquid impervious back sheet 1 is equivalent to an outer part of the subject invention. In addition, the absorbent body 3 is equivalent to an inner part of the present invention.

The liquid impervious back sheet 1 may use a polyethylene film, or may use a sheet with both moisture permeability and water imperviousness, from the viewpoint of stuffiness prevention. The water-impervious and moisture-permeable sheet may be a microporous sheet obtained by melting and kneading an inorganic filling material into an olefin resin such as polyethylene, polypropylene or the like to thereby form a sheet and then extending the sheet in a uniaxial or biaxial direction. A weight per unit area of the back sheet 1 is preferably 18 to 22 g/m², and a thickness of the same is preferably 0.1 to 0.5 mm.

The outer sheet 12 may use any of various nonwoven fabrics. Raw materials for constituting the nonwoven fabric may be any of synthetic fibers based on olefin such as polyethylene or polypropylene, polyester, amide or the like, recycled fibers such as rayon or cupra, natural fibers such as cotton. A fiber basis weight of a nonwoven fabric for use in the outer sheet 12 is preferably 15 to 20 g/m², and a thickness of the same is preferably 0.065 to 0.070 mm.

The liquid pervious top sheet 2 uses a porous or nonporous nonwoven fabric, a perforated plastic sheet, or the like. Raw materials for constituting the nonwoven fabric may be any of synthetic fibers based on olefin such as polyethylene or polypropylene, polyester, amide or the like, recycled fibers such as rayon or cupra, natural fibers such as cotton. A fiber basis weight of a nonwoven fabric for use in the liquid pervious top sheet 2 is preferably 18 to 20 g/m², and a thickness of the same is preferably 0.1 to 0.5 mm.

Basically the absorbent body 3 uses accumulated pulp fibers, an assembly of filaments of cellulose acetate or the like, or a nonwoven fabric, to which high-absorbent polymers may be mixed and fixed as required. If necessary, the absorbent body 3 may be wrapped with crepe paper (not shown). The absorbent body 3 can be formed in any of appropriate shapes, and preferably has the shape of a sandglass as illustrated or a rectangular or the like, which extends from the front to back sides of the crotch portion. The absorbent body 3 has desirably a basis weight of pulp of about 200 to 250 g/m² and a thickness of about 3 to 10 mm. In addition, a desired basis weight of high-absorbent resin is about 45 to 55 g/m². If a content of high-absorbent resin is too low, it is impossible to provide sufficient absorbent performance. In contrast, if a content of high-absorbent resin is too high, the absorbent body 3 is likely to be twisted or broken because there is no entanglement between pulp fibers.

The liquid impervious back sheet 1 has the shape of an approximate rectangle that extends outward beyond the circumference of the absorbent body 3. Barrier sheets 4 have widthwise outside sections 4$x$ stuck to the entire front-back inner surface of the liquid impervious back sheet 1 at extending side portions, thereby to form side flap sections SF in the absence of the absorbent body 3. The barrier sheets 4 have widthwise central sections 4$c$ extending over the top sheet 2, and have elongated elastic members 4G fixed in a stretched state in the front-back direction with a hot-melt adhesive or the like to ends of the sections 4$c$ in the center in the width direction. Those elongated elastic members 4G and elongated elastic members 13 described later may be formed in the shape of a thread, a string, a band, or the like, and use any of common materials such as styrene-based rubber, olefin-based rubber, urethane-based rubber, ester-based rubber, polyurethane, polyethylene, polystyrene, styrene-butadiene, silicon, polyester, or the like.

The liquid pervious top sheet 2 has the shape of a sandglass slightly larger than the absorbent body 3. The liquid pervious top sheet 2 has sections extending outward slightly beyond the side edges of the absorbent body 3, which are interposed between the barrier sheets 4 and the liquid impervious back sheet 1 and are adhered to the liquid impervious back sheet 1 with a hot-melt adhesive or the like. In FIGS. 8 and 9, those adhered sections are shown in a dot pattern. The barrier sheets 4 may use a plastic sheet or a melt-blown nonwoven fabric as a material, and preferably use a water-repellent nonwoven fabric by silicon or the like, from the viewpoint of a favorable texture.

If an outer surface of the liquid impervious back sheet 1 is covered with a nonwoven fabric, the outer nonwoven fabric may extend outward beyond the circumference of the absorbent body 3, instead of the liquid impervious back sheet 1, thereby to form the side flap sections SF in the absence of the absorbent body 8 together with the side portions of the barrier sheets 4. In this case, the liquid impervious back sheet 1 may not extend to the side flap sections SF so as to have the same shape as that of the top sheet 2.

As shown in FIGS. 8 and 9, the two barrier sheets 4 and 4 are fixed in such a manner that the widthwise outside sections 4$x$ are fixed to the entire front-back inner surface of the article in an undetachable manner (in the illustrated embodiment, the top surface of the top sheet 2 and the inner surface of the back sheet 1); the widthwise central sections 4$c$ are fixed at both front-back ends to the inner surface of the article (in the illustrated embodiment, the top surface of the top sheet 2) in a detachable manner; and the widthwise central sections 4$c$ are not fixed between the both front-back ends to the inner surface of the article (in the illustrated embodiment, the top surface of the top sheet 2). As shown in FIG. 9, those unfixed portions constitute barrier parts that can be erected with respect to the inner surface of the article (in the illustrated embodiment, the top surface of the top sheet 2). The barrier parts have base ends 4$b$ for electing located in boundaries between the widthwise outside fixed portions 4$x$ and the inner portions 4$c$ in the barrier sheets 4.

At the both front-back ends of the disposable diaper 100, the liquid impervious back sheet 1 and the liquid pervious top sheet 2 extend toward both front-back sides beyond the front-back ends of the absorbent body 3, thereby to form end flap sections EF in the absence of the absorbent body 3. The back-side end flap section EF has a plurality of, three in the illustrated embodiment, threadlike elastic members 7, 7 . . . disposed in the width direction. The threadlike elastic members 7 may be any of common materials such as styrene-based rubber, olefin-based rubber, urethane-based rubber, ester-based rubber, polyurethane, polyethylene, polystyrene, styrene-butadiene, silicon, polyester, or the like.

In addition, the both side flap sections SF of the back side B1 have fastening tapes 5 and 5 projecting sideward around the waist portions. In addition, the ventral side F1 of the disposable diaper 100 has a front target tape 6 on a surface thereof around the waist portion. The fastening tapes 5 have join pieces 8$a$ fastened to the front target tape 6 so that the disposable diaper 100 is attached to the body of the wearer.

Each of the fastening tapes 5 in this embodiment as shown in FIG. 10, is attached to the disposable diaper 100 at an inner end of a fastening base sheet 8, and has the two join pieces 8$a$ and 8$a$ at a leading end thereof which extend from an outer edge and project sideward in a vertically aligned manner. In addition, the fastening tapes 5 each have a perforated line 10 formed inward from the outer edge thereof in a horizontal direction with respect to the fastening base sheet 8 between the join pieces 8$a$ and 8$a$. However, the fastening tapes 5 are not limited to the foregoing arrangement and may be any of publicly known fastening tapes. The fastening base sheet 8 may use any of various sheet materials, and preferably uses a single-layer or multi-layer nonwoven fabric with a basis weight of 40 to 80 g/m². A preferred processing method for the nonwoven fabric is a spun-bonding method with an excellent strength property. The join pieces 8$a$ and 8$a$ have on inner surfaces thereof (the liquid pervious top sheet 2 side) hook tapes (hook members of mechanical fasteners) 9 and 9 having a large number of hook-shaped projections on surfaces thereof. The hook-shaped projections can be joined to front target tapes 6 (loop materials of mechanical fasteners) with surfaces of which the hook-shaped projections engage in a detachable manner.

Characteristically, a plurality of elongated elastic members 13 is provided on the under side of the absorbent body 3 at the both sides of the diaper 100 in the width direction so as to extend from the ventral side portion F1 to the back side portion B1 and to draw bulging lines at the crotch portion C1 toward the center in the width direction. In this embodiment, the elongated elastic members 13 are fixed using an adhesive between the outer sheet 12 and the back sheet 1, and alternatively the elongated elastic members 13 may be fixed to the inner surface of the back sheet 1.

Particularly in this embodiment, a plurality of outer elastic members 13$s$ (five in the illustrated example) is provided at the side flap sections SF so as to extend along a leg portion of a narrow part. In addition, a plurality of inner elastic members 13$i$ (three in the illustrated example) is also provided at the side flap sections SF, having start and end points at the side flap sections SF on the ventral and back sides. The inner elastic members 13*i* draw bulging lines and extend toward the center at the crotch portion C1 so as to overlap the absorbent body 3 (if the absorbent pad 200 is appropriately arranged, it is preferred that the inner elastic members 13*i* also overlap the absorbent body 23 of the absorbent pad 200).

The inner elastic members 13*i* are shifted outward in the width direction with distance from the crotch portion C1. The inner elastic members 13*i* are arranged so as to come close to the outer elastic members 13*s* and then extend along the outer elastic members at specific intervals.

At the crotch portion C1, a minimum widthwise interval d1 between the inner elastic member 13*i* on one widthwise side and the inner elastic member 13*i* on the other widthwise side can be decided as appropriate, and preferably is 60 to 65 mm. If the interval d1 is too small or too large, it is difficult to hold the absorbent pad 200 at appropriate positions on the both sides in the width direction. A front-back area L2 for arrangement of the inner elastic members 13*i* (applicable also to the outer elastic members 13*s*) ranges preferably from a position of 280 to 310 mm frontward with respect to the front-back middle of the diaper to a position of 180 to 300 mm backward with respect to the front-back middle of the diaper. In addition, a front-back area L3 for overlapping of the inner elastic members 13*i* and the absorbent body 3 ranges preferably from a position of 230 to 300 mm frontward with respect to the front-back middle of the diaper to a position of 150 to 180 mm backward with respect to the front-back middle of the diaper. Further, a front-back area L4 for overlapping of the inner elastic member 13*i* and the absorbent pad 200 ranges preferably from a position of 130 to 180 mm frontward with respect to the front-back middle of the diaper to a position of 10 to 80 mm backward with respect to the front-back middle of the diaper.

The elongated elastic members 13*s* and 13*i* may use synthetic or natural rubber having any of appropriate shapes such as a thread, a string, a band, and the like. If synthetic rubber is used for the elongated elastic members, the elongated elastic members have preferably a fineness of about 940 to 1,240 dtex and an extension ratio of about 150 to 250%. In addition, preferably, about three to five outer elastic members 13*s* are provided in parallel at intervals of 5 to 10 mm, and about three to five inner elastic members 13*i* are provided in parallel at intervals of 3 to 15 mm.

Characteristically, the inner elastic members 13*i* are arranged using an unfixed structure of the present invention. Specifically, in this embodiment, the liquid impervious back sheet 1 is stuck to the inside of the outer sheet 12 to thereby form the outer part. The inner elastic members 13*i* are fixed in a stretched state between the two sheets 1 and 12. The outer part has a section designated as an unfixed section 14 where the back sheet 1 and the outer sheet 12 are not fixed, corresponding to a first portion P1 at the longitudinal intermediate of the inner elastic members 13*i*. In addition, the outer part has a section designated as a fixed section, corresponding to a second portion P2 on the both longitudinal sides of the unfixed section 14, where the back sheet 1 and the outer sheet 12 are fixed (all the section other than the unfixed section 14, as shown in a dot pattern). The unfixed section 14 with the inner elastic members 13*i* is not fixed to the back sheet 1 or the outer sheet 12, and the fixed section with the inner elastic members 13*i* are fixed to the back sheet 1 and the outer sheet 12, as shown in FIG. 9. The two sheets 1 and 12 can be fixed at the fixed section with a hot-melt adhesive or the like, or through welding by ultrasonic sealing or heat sealing.

Alternatively, the unfixed section 14 with the inner elastic members 13*i* may be fixed only to the outer sheet 12 and be unfixed to the back sheet 1 as shown in FIG. 12. This produces an advantage that the inner elastic members 13*i* can be arranged even at the unfixed section 14 in an arbitrary shape such as a curvature or the like, but decreases the degree of freedom of the inner elastic members 13*i* as compared with the embodiment shown in FIG. 9. At the time of manufacture, a comb shaped gun type applicator or a SureWrap™ nozzle, for example, can be used to apply an adhesive to each of the elastic members, the elastic members are fixed in a stretched state to the outer sheet 12, and the back sheet 1 is joined to the inner surface of the outer sheet 12 at a predetermined fixed section and is not joined to the inner surface of the outer sheet 12 at the unfixed section 14.

In any of the foregoing embodiments, the inner elastic members 13*i* can move singly or together with the outer sheet 12 in the unfixed section 14, with respect to the back sheet 1. Accordingly, even if the back sheet 1 or the absorbent body 3 is deformed by body movements, for example, the inner elastic members 13*i* are not affected by the deformation and can be kept in a properly stretched state, thereby to press the absorbent pad 200 on the inner side against the body of the wearer, in a proper position or in a properly stretched state. As a result, the absorbent pad 200 is less prone to be displaced or deformed (contracted, twisted, or the like) by body movements of the wearer, which reduces occurrence of leakage resulting from such a displacement or the like.

The unfixed section 14 can be decided as appropriate as far as the section is located in the longitudinal intermediate of the inner elastic members 13*i*. In the embodiment shown in FIG. 6, for example, the unfixed section 14 constitutes a rectangular region that extends in the front-back direction from the back side portion B1 in proximity to the crotch portion C1 through the crotch portion C1 to the front-back middle in the ventral side portion F1, and extends in the width direction from one side edge of the absorbent pad 200 to the other side edge of the same. Alternatively, as shown in FIGS. 13 and 14, a fixed section may be provided between the inner elastic members 13*i* on one widthwise side and the inner elastic members 13*i* on the other widthwise side, and unfixed sections may be independently provided on the both widthwise sides of the fixed section.

Specifically, in the foregoing cases, the unfixed section 14 preferably ranges from a position of 130 to 200 mm frontward with respect to the front-back middle of the diaper to a position of 10 to 30 mm backward with respect to the front-back middle of the diaper. FIGS. 6 and 13 show a front-back area with reference numeral 14*f* ranging from the front-back middle of the diaper to a front end of the unfixed section 14, and show a front-back area with reference numeral 14*b* ranging from the front-back middle of the diaper to the back end of the unfixed section 14. Those areas cover the crotch portion C1 and its front-back neighboring portions. Those areas are sandwiched between the both legs of the wearer, and are subjected to forces from various directions caused by twisting or the like mainly due to widthwise contraction, and therefore the inner elastic members 13*i* are likely to be displaced from the proper positions in those areas. Accordingly, by setting the unfixed section 14 in those areas, it is possible to prevent effectively displacement or deformation of the absorbent pad 200.

Alternatively, as shown in FIG. 15, the unfixed sections 14 are preferably provided so as to correspond to right and left inguinal regions and their neighboring areas, and right and left gluteal sulci and their neighboring areas. The unfixed sections 14 provided so as to correspond to the right and left inguinal regions and their neighboring areas and the unfixed sections 14 provided so as to correspond to right and left gluteal sulci and their neighboring areas, may be separated from each other as in the illustrated embodiment or may be made continuous. More specifically, those unfixed sections 14 are positioned in a front-back area of ±10 to 40 mm from a position of 170 to 210 mm frontward with respect to the front-back middle of the diaper and in a front-back area of ±20 to 30 mm from a position of 20 to 50 mm backward with respect to the front-back middle of the diaper. The front-back range of the front-side unfixed sections 14 is shown with reference numeral 14m, and the front-back range of the back-side unfixed sections 14 is shown with reference numeral 14n. The diaper may have relatively large shape changes at the inguinal regions and their neighborhood areas, and may have large extension or contraction at the gluteal sulci and their neighborhood areas. Accordingly, by setting the unfixed sections 14 in those areas, it is possible to prevent effectively displacement or deformation of the absorbent pad 200.

In the embodiment shown in FIG. 15, the right and left unfixed sections 14 are made independent from each other as in the embodiment shown in FIG. 13. Alternatively, the right and left unfixed sections 14 may be unified as in the embodiment shown in FIG. 6. Further, the unfixed sections 14 in the embodiment of FIG. 6 or 13 may extend in the front-back direction to the inguinal regions, the gluteal sulci, and their neighboring areas.

Meanwhile, a width of the unfixed section 14 orthogonal to the inner elastic member 13i (hereinafter referred to as unfixed width) determines movement of the inner elastic member 13i. The unfixed width may constitute a full width of the inner elastic member 13i (or a total of widths of a plurality of elastic members if the elastic members are provided together) or may be wider than the full width. In the former case, the unfixed section 14 becomes narrow to such an extent that the inner elastic member 13i does not move in a direction orthogonal to the longitudinal direction of the elastic member, and therefore the inner elastic member 13i can move virtually only in the longitudinal direction. This provides an advantage that the diaper is less prone to be brought into an unbalanced stretched state. In contrast, if the unfixed width 14w is made wider than the full width of the inner elastic member 13i, the diaper is less prone to be brought into an unbalance stretched state and also the inner elastic member 13i can preferably move to a proper position in the unfixed section. Accordingly, it is preferred that the unfixed section 14 extends by a distance equal to or more than the full width of the inner elastic member 13i in the direction orthogonal to the inner elastic member 13i, on either or both of the widthwise outside and the widthwise inside with respect to the inner elastic member 13i running in the unfixed section 14.

More specifically, in each of the embodiments shown in FIGS. 6 and 13, the unfixed section 14 preferably extends 20 to 80 mm in the direction orthogonal to the inner elastic member 13i, on either or both of the widthwise outside and the widthwise inside with respect to the inner elastic member 13i running in the unfixed section 14 (if a plurality of elastic members 13i is provided, the widthwise outside with respect to the inner elastic member 13i located on a widthwise outermost-side and the widthwise inside with respect to the inner elastic member 13i located on a widthwise innermost-side. This also applies to the following descriptions). In the embodiment shown in FIG. 15, the unfixed section 14 preferably extends 20 to 60 mm in the direction orthogonal to the inner elastic member 13i running in the unfixed section 14 on either or both of the widthwise outside and the widthwise inside with respect to the inner elastic member 13i in a front-back area of ±10 to 40 mm from a position of 170 to 210 mm frontward with respect to the front-back middle of the diaper, and the unfixed section 14 preferably extends 60 to 80 mm in the direction orthogonal to the inner elastic member 13i running in the unfixed section 14 on either or both of the widthwise outside and widthwise inside with respect to the inner elastic member 13i in a front-back area off 20 to 30 mm from a position of 20 to 50 mm backward with respect to the front-back middle of the diaper. FIGS. 9, 14, and 15 show an extending distance of the unfixed section 14 with reference numeral 14s on the widthwise outside of the inner elastic member 13i, and show an extending distance of the unfixed section 14 with reference numeral 14c on the widthwise inside with respect to the inner elastic member 13i.

(Other Embodiments)

(a) Although the foregoing embodiments each employ a tape-type disposable diaper, the present invention is directed to various diapers in which an elongated elastic member is fixed in a stretched state between inner and outer sheets on both widthwise sides so as to extend from the ventral side portion through the crotch portion to the back side portion. Therefore, the present invention is also applicable to under-pants-type diapers as far as the foregoing condition is satisfied.

(b) Although in each of the foregoing embodiments, the liquid impervious back sheet 1 constitutes an inner sheet and the outer sheet 12 constitutes an outer sheet, the inner and outer sheets may be used without particular limitation as far as those sheets are located on the under side of the absorbent body 3. For example, if the outer sheet 12 is formed by a plurality of sheets stuck together, an inner one of those sheets may be used as an inner sheet and an outer one of the same as an outer sheet.

INDUSTRIAL APPLICABILITY

The present invention is used for a combination of an absorbent pad and a disposable diaper.

Figure 1:
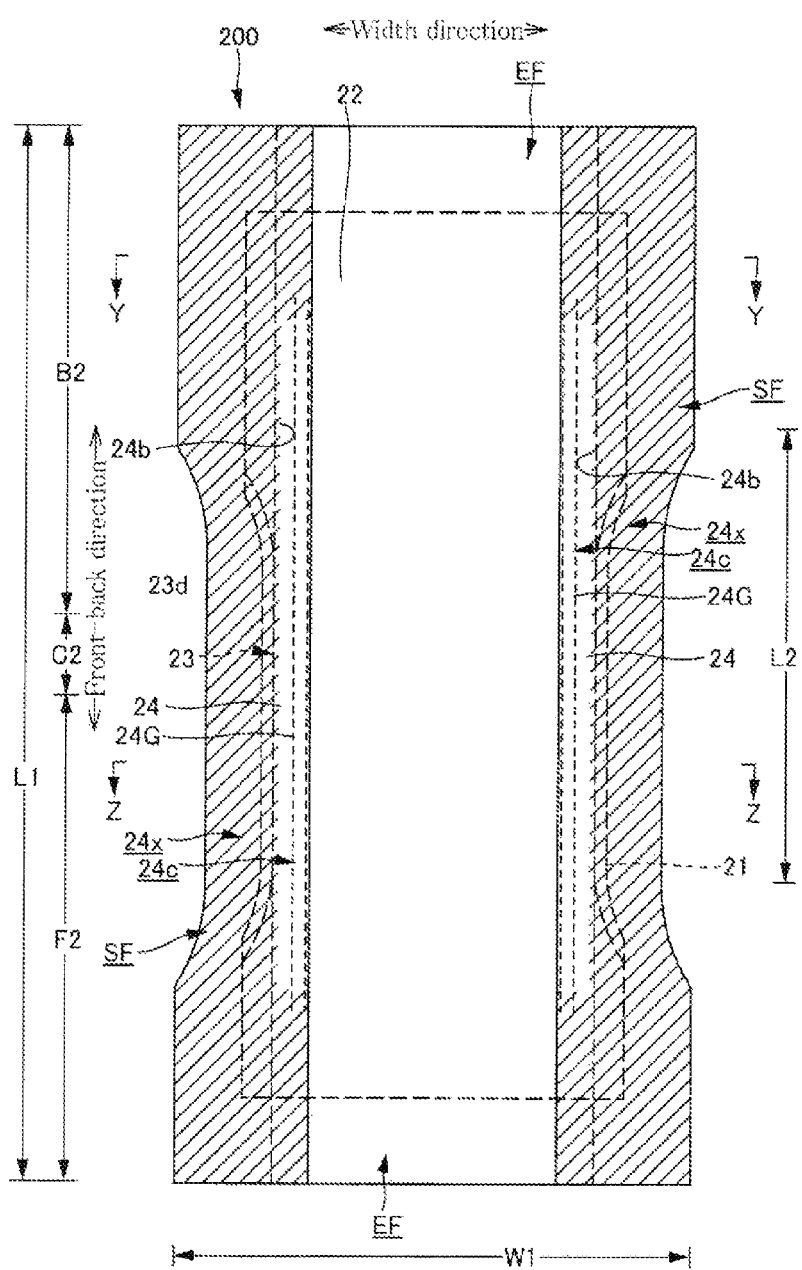
FIG. 1 is a plane view of an inner surface of an opened absorbent pad.
Figure 2:
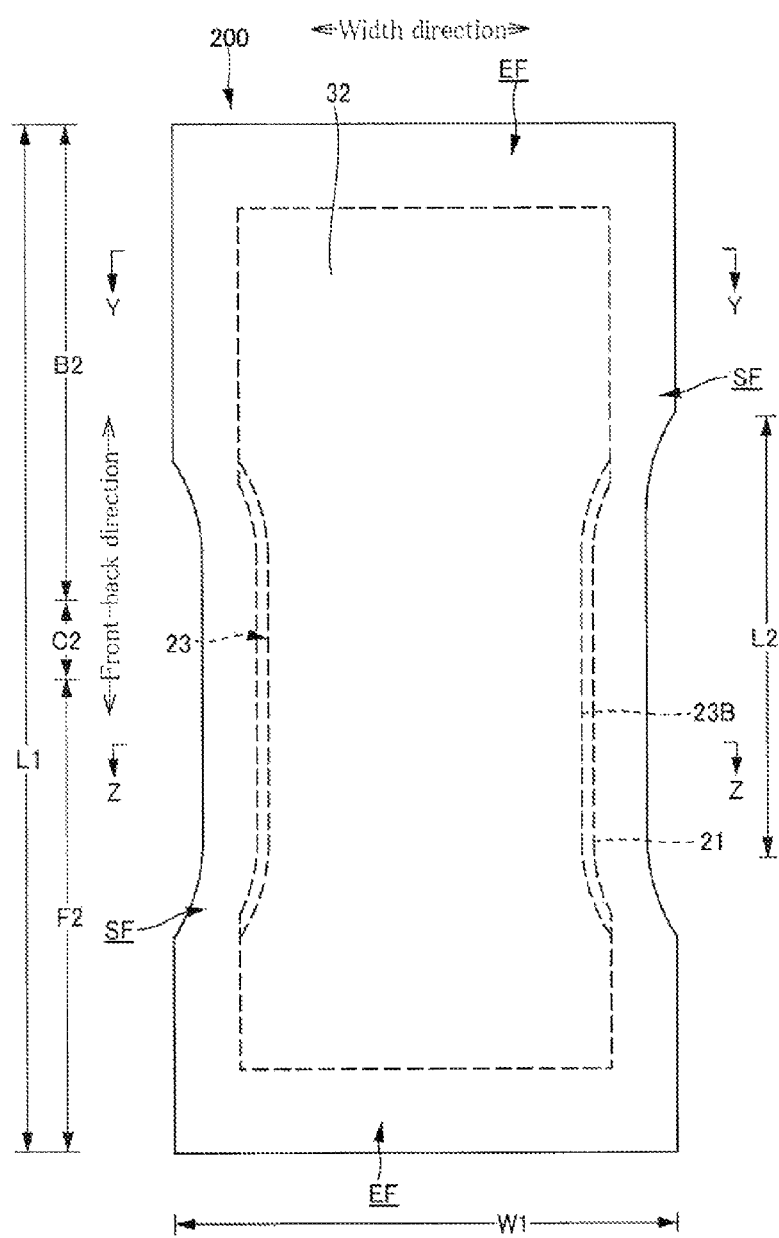
FIG. 2 is a plane view of an outer surface of the opened absorbent pad.
Figure 3:
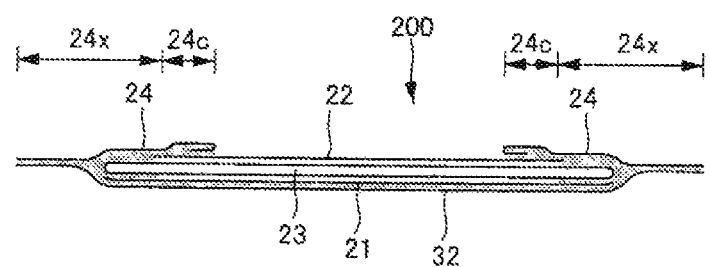
FIG. 3 is a cross-section view of FIG. 1 along Y-Y.
Figure 4:
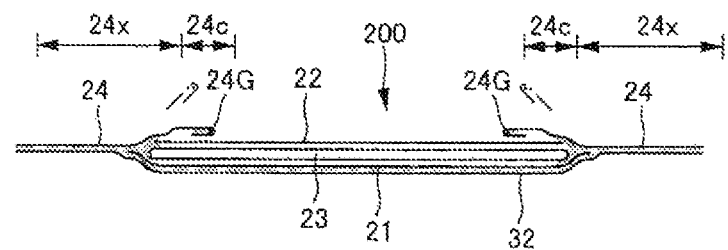
FIG. 4 is a cross-section view of FIG. 1 along Z-Z.
Figure 5:
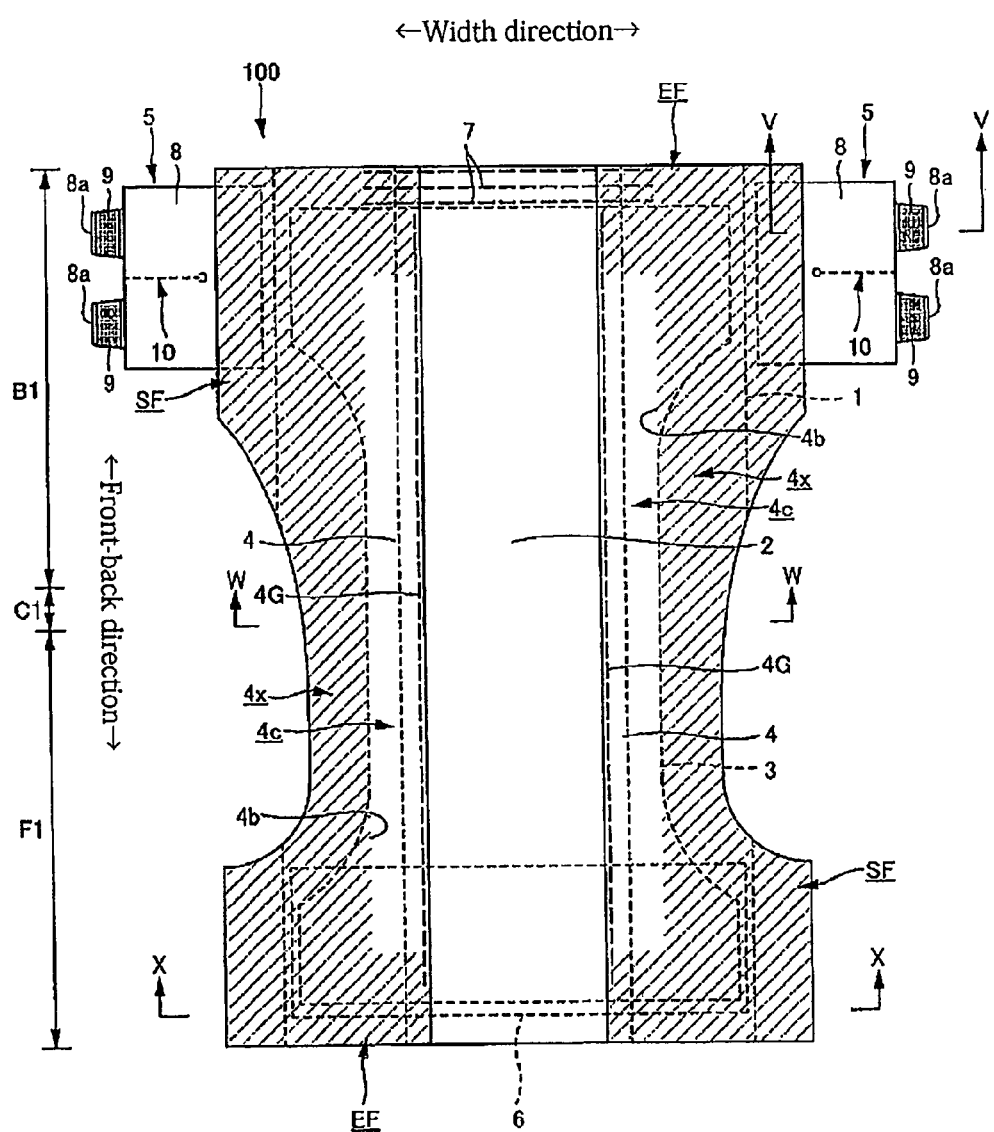
FIG. 5 is a plane view of an inner surface of an opened tape-type disposable diaper.
Figure 6:
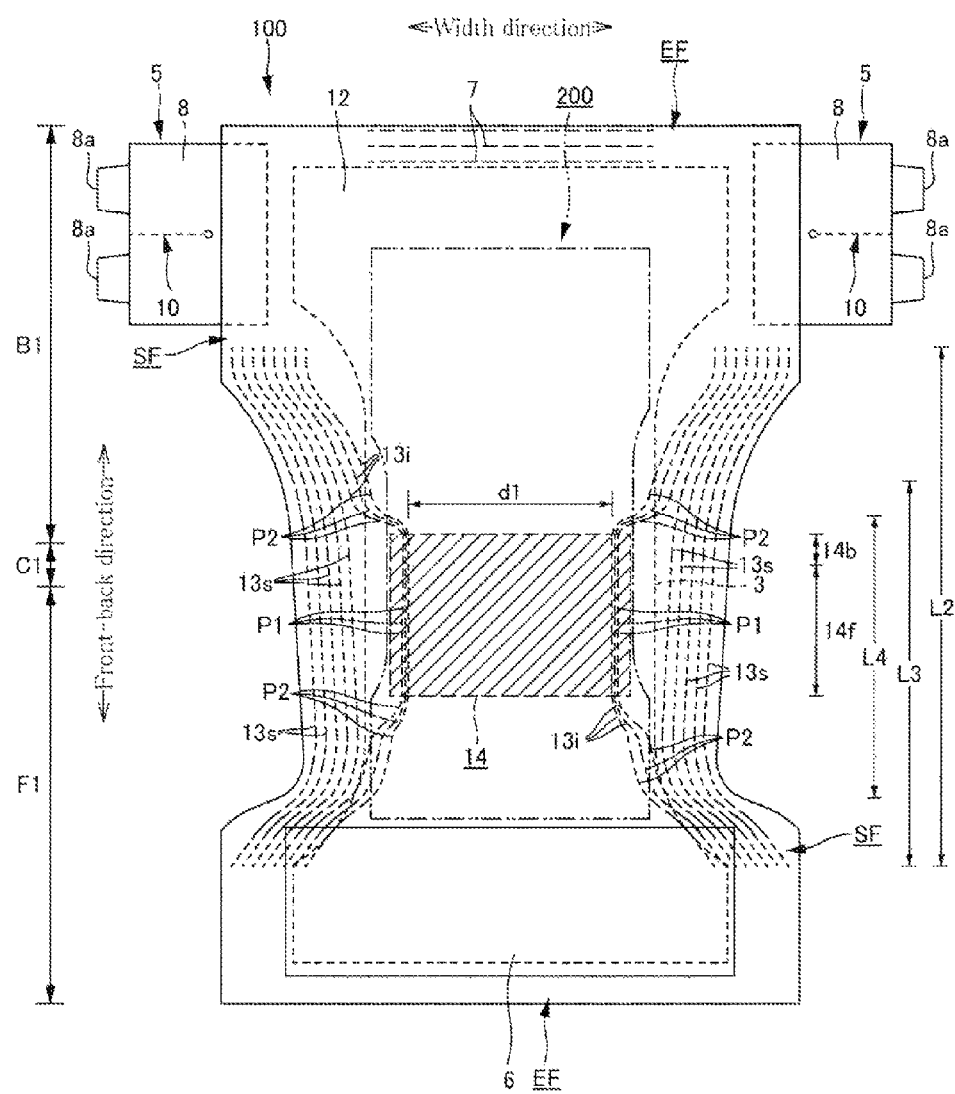
FIG. 6 is a plane view of an outer surface of the opened tape-type disposable diaper.
Figure 7:
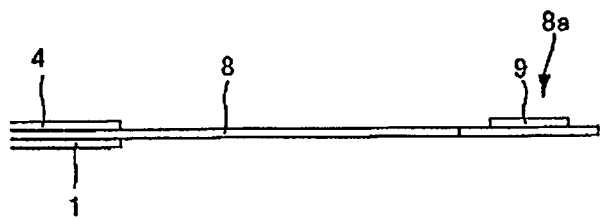
FIG. 7 is a cross-section view of FIG. 5 along V-V.
Figure 8:
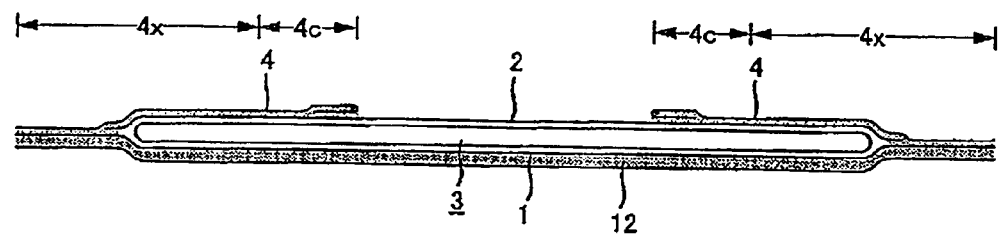
FIG. 8 is a cross-section view of FIG. 5 along W-W.
Figure 9:
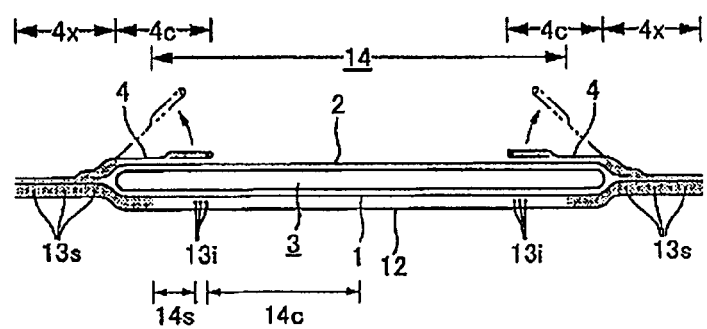
FIG. 9 is a cross-section view of FIG. 5 along X-X.
Figure 10:
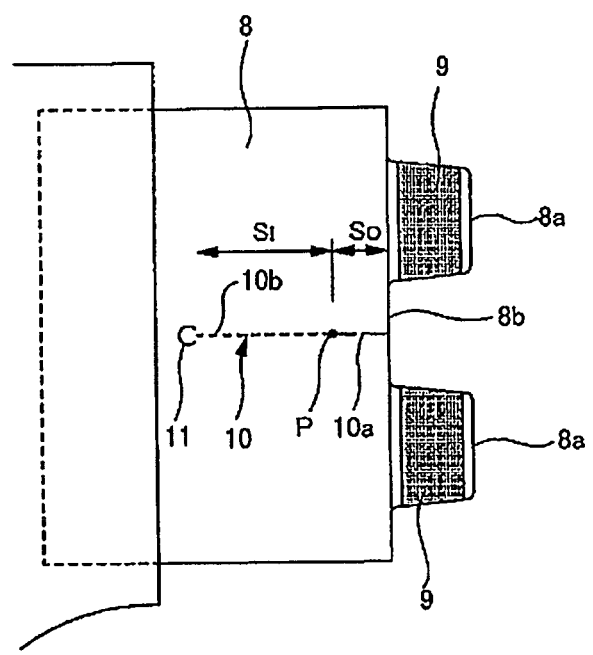
FIG. 10 is an enlarged plane view of major components.
Figure 11:
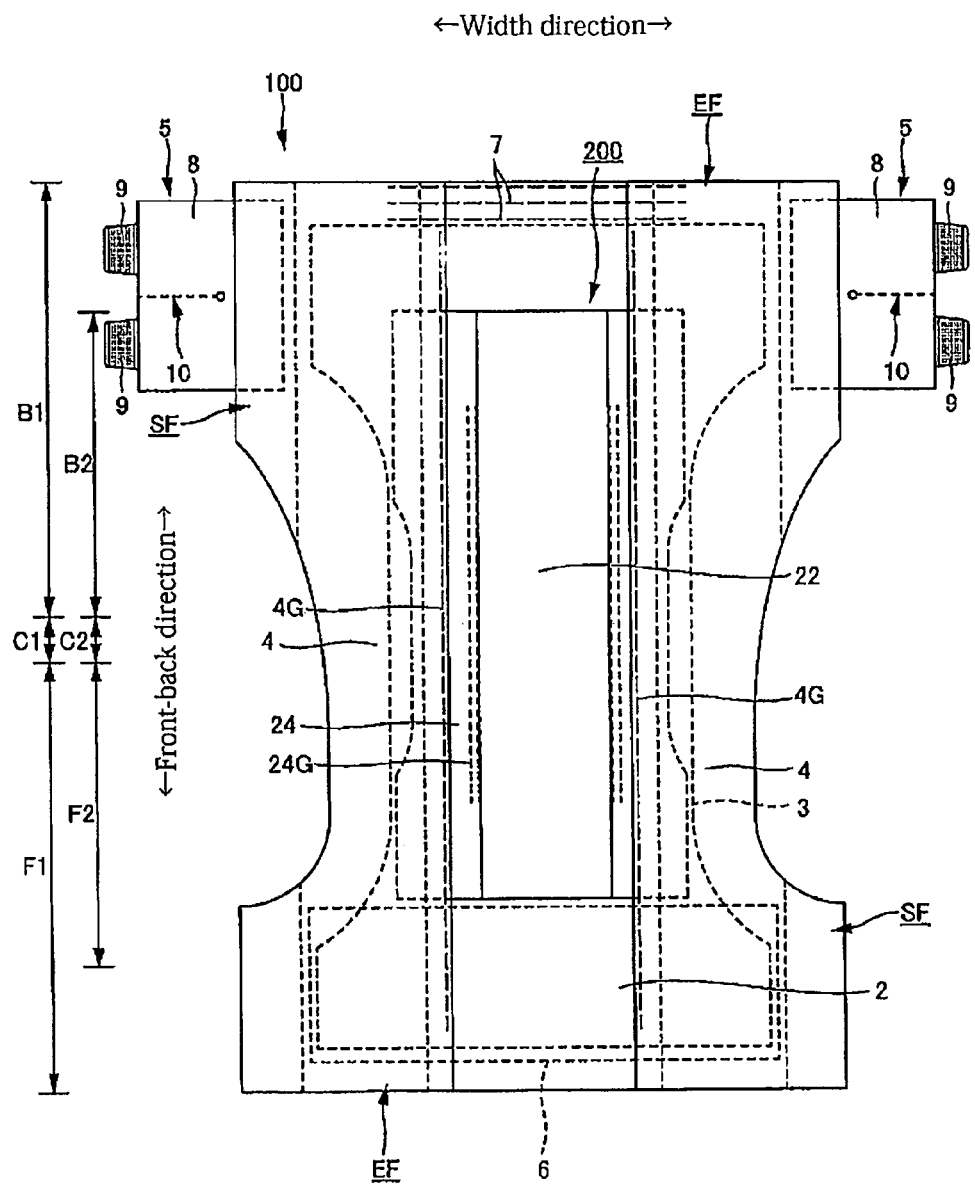
FIG. 11 is a plane view of the inner surface of the opened tape-type disposable diaper with the absorbent pad attached.
Figure 12:
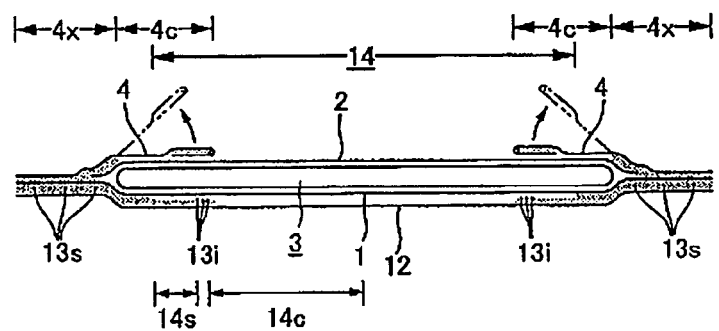
FIG. 12 is a cross-section view of another embodiment equivalent to FIG. 5 along W-W.
Figure 13:
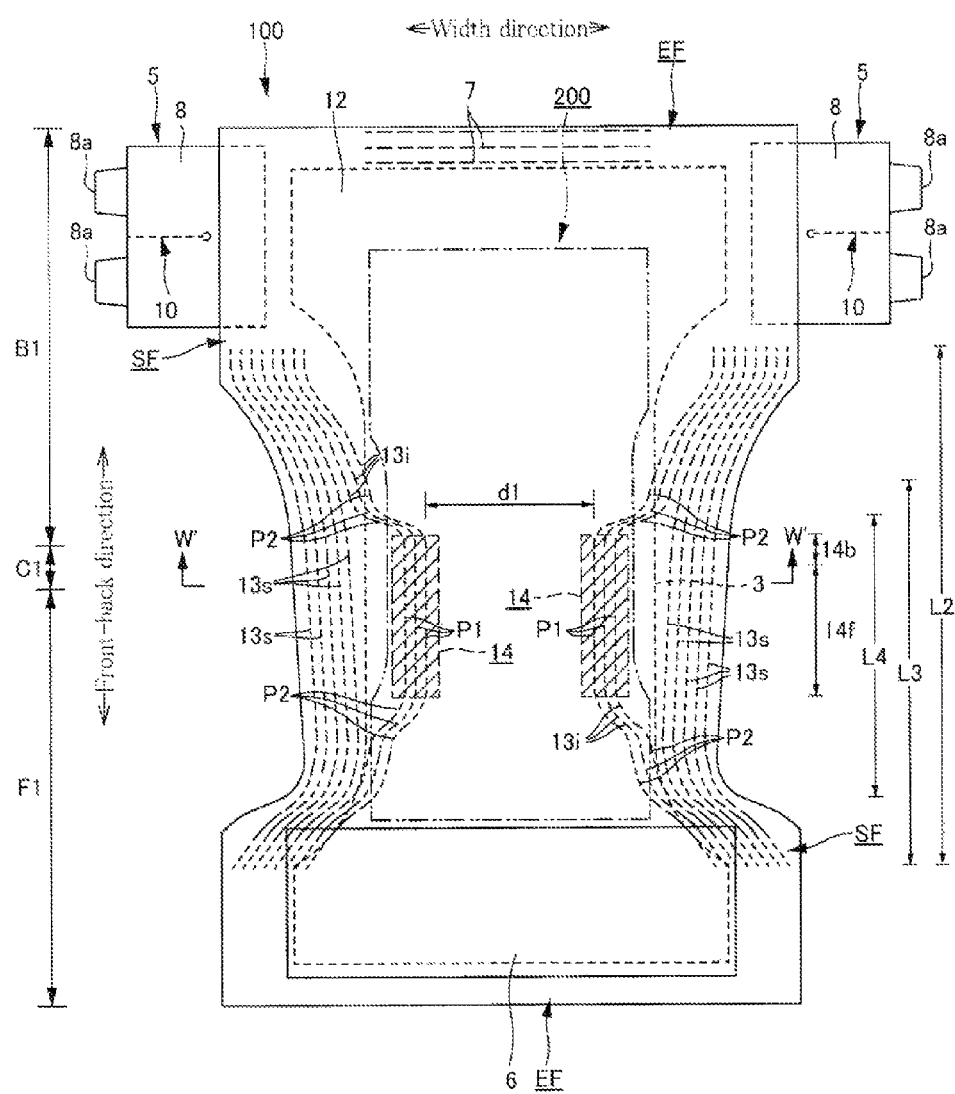
FIG. 13 is a plane view of an outer surface of another opened tape-type disposable diaper.
Figure 14:
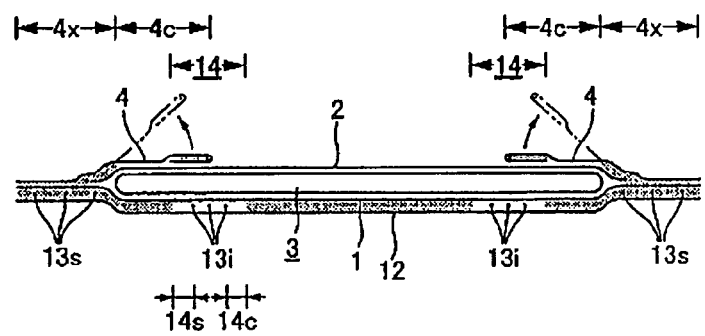
FIG. 14 is a cross-section view of FIG. 13 along W'-W'.
Figure 15:
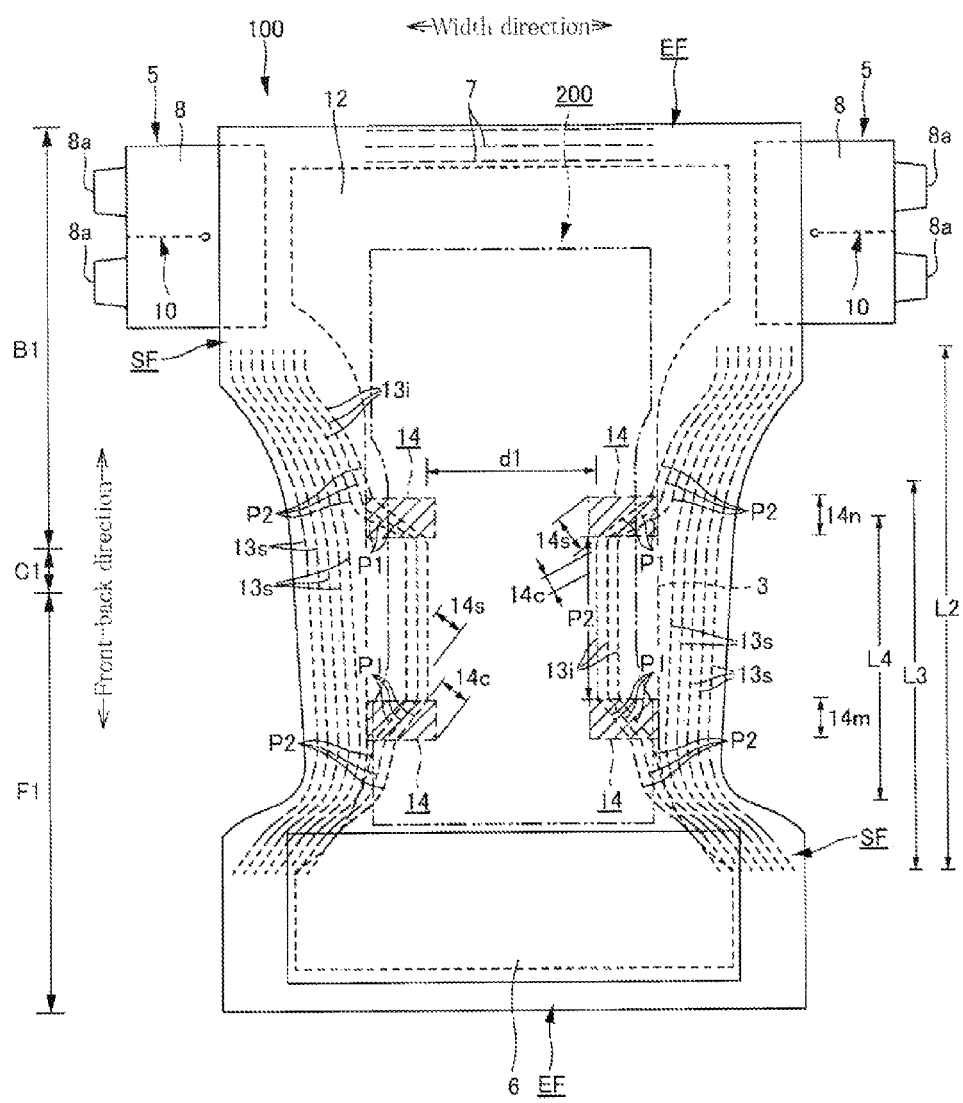
FIG. 15 is a plane view of an outer surface of still another opened tape-type disposable diaper.

DESCRIPTION OF THE REFERENCE NUMERALS 1, 21 . . . . Liquid impervious back sheet, 2, 22 . . . . Liquid pervious top sheet, 3, 23 . . . . Absorbent body, 4, 24 . . . .

Barrier sheet, 5 . . . . Fastening tape, 6 . . . . Target tape, 7 . . . . Elastic member, 8 . . . . Base sheet, 9 . . . . Hook tape, 10 . . . . Perforated line, 14 . . . . Unfixed section, 12, 32 . . . . Outer sheet, 13*i*, 13*s*, 33, 34 . . . . Elastic member, 100 . . . . Tape-type disposable diaper, 200 . . . . Absorbent pad What invention claimed is:

1. A disposable diaper comprising:
    an outer part having a crotch portion and ventral and back side portions extending to front and back sides of the crotch portion, respectively, the outer part comprising an inner sheet and an outer sheet, and at least a portion of the inner sheet being fixed to the outer sheet, wherein the inner sheet is fixed to the outer sheet in the ventral and back side portions forming first and second fixed sections, wherein the inner sheet between the first and second fixed sections is an unfixed section;
    an inner part provided on an inner surface of the outer part, the inner part having an absorbent body at the crotch portion, and
    an elongated elastic member fixed in a stretched state between the inner and outer sheets on both sides in a width direction so as to extend from the ventral side portion through the crotch portion to the back side portion, wherein the elongated elastic member is continuously provided from the first fixed section to the second fixed section, and wherein the unfixed section is between the first and second fixed sections,
    wherein the inner sheet comprises an unfixed section between the first and second fixed sections, and in the unfixed section, the elongated elastic member is not fixed to the inner or outer sheet, and
    wherein, in the fixed sections in which the inner and outer sheets are fixed, the elongated elastic member is fixed to the inner and outer sheets.

2. The disposable diaper according to claim 1, wherein the unfixed section is continuously provided ranging from a position of 150 to 250 mm frontward with respect to a center of the diaper in a front-back direction to a position of 10 to 160 mm backward with respect to the center of the diaper in the front-back direction.

3. The disposable diaper according to claim 1, wherein the unfixed section is continuously provided in the front-back direction, in a front-back area of ±10 to 40 mm with reference to a position of 170 to 210 mm frontward with respect to the center of the diaper in the front-back direction, and the other unfixed section is continuously provided in a front-back area of ±20 to 30 mm with reference to a position of 20 to 50 mm backward with respect to the center of the diaper in the front-back direction.

4. The disposable diaper according to any one of claims 1 to 3, wherein the unfixed section extends, on at least one of a widthwise outside and a widthwise inside with respect to an elongated elastic member running in the section, in a direction orthogonal to the elongated elastic member by a distance equal to or more than a full width of the elongated elastic member.

5. The tape-type disposable diaper according to any one of claims 1 to 3, wherein a fastening tape is projected from both sides in the width direction of at least one of the ventral and back side portions, for connection with the other portion in a detachable manner.

6. An absorbent article comprising:
    the disposable diaper according to any one of claims 1 to 3;
    an absorbent pad having front and back portions extending to front and back sides of the crotch portion, respectively, and the absorbent body formed of a fiber assembly at a main body part surrounded by a circumferential portion, wherein
    the absorbent pad is disposed in alignment with the crotch portion on an inner surface of the inner part of the disposable diaper.

\* \* \* \* \*